US011712227B2

United States Patent
Murakami

(10) Patent No.: US 11,712,227 B2
(45) Date of Patent: Aug. 1, 2023

(54) ULTRASOUND PROBE, CONTROL METHOD OF ULTRASOUND PROBE, AND ULTRASOUND PROBE INSPECTION SYSTEM

(71) Applicant: FUJIFILM Corporation, Tokyo (JP)

(72) Inventor: Hiroshi Murakami, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 386 days.

(21) Appl. No.: 17/035,916

(22) Filed: Sep. 29, 2020

(65) Prior Publication Data

US 2021/0007718 A1 Jan. 14, 2021

Related U.S. Application Data

(63) Continuation of application No. PCT/JP2019/010644, filed on Mar. 14, 2019.

(30) Foreign Application Priority Data

Apr. 5, 2018 (JP) ................. 2018-073183

(51) Int. Cl.
*A61B 8/00* (2006.01)
*G08C 23/00* (2006.01)
*G16H 40/67* (2018.01)

(52) U.S. Cl.
CPC ............ *A61B 8/58* (2013.01); *A61B 8/4209* (2013.01); *A61B 8/54* (2013.01); *A61B 8/565* (2013.01); *G08C 23/00* (2013.01); *G16H 40/67* (2018.01)

(58) Field of Classification Search
CPC ........... A61B 8/58; A61B 8/4209; A61B 8/54; A61B 8/565; A61B 8/4472; A61B 8/56;
(Continued)

(56) References Cited

U.S. PATENT DOCUMENTS 4,453,409 A 6/1984 Naumann, Jr. et al.
2010/0286527 A1* 11/2010 Cannon .................... A61B 8/42
600/459

(Continued)

FOREIGN PATENT DOCUMENTS

JP S58-46950 A 3/1983
JP 2013-015407 A 1/2013
JP 2015-211726 A 11/2015

OTHER PUBLICATIONS

International Search Report issued in PCT/JP2019/010644; dated May 28, 2019.

(Continued)

*Primary Examiner* — Yi-Shan Yang
*Assistant Examiner* — Alexei Bykhovski
(74) *Attorney, Agent, or Firm* — Studebaker & Brackett PC

(57) ABSTRACT

An ultrasound probe includes a housing; a transducer array housed in the housing; a transmission/reception unit which is housed in the housing, transmits ultrasonic wave from the transducer array, and generates a sound ray signal on the basis of a reception signal acquired by the transducer array; an image information data generation unit which is housed in the housing, and generates image information data on the basis of the sound ray signal generated by the transmission/reception unit; a wireless communication unit which is housed in the housing, and wirelessly transmits the image information data generated by the image information data generation unit; a light emission unit which is housed in the housing, and emits light to an outside of the housing; and a light emission control unit which is housed in the housing, and causes the light emission unit to emit light in synchronization with a transmission timing of the ultrasonic wave (Continued)

by the transmission/reception unit in a case of a manufacturing inspection.

16 Claims, 9 Drawing Sheets

(58) Field of Classification Search
CPC ...... A61B 8/4444; G08C 23/00; G16H 40/67; G16H 30/20
See application file for complete search history.

(56) References Cited

U.S. PATENT DOCUMENTS

| 2012/0215280 | A1* | 8/2012 | Peddicord | A61H 19/00 |
| | | | | 607/116 |
| 2016/0228090 | A1* | 8/2016 | Boctor | G01S 15/899 |
| 2021/0064334 | A1* | 3/2021 | Hidai | G06F 3/167 |

OTHER PUBLICATIONS

International Preliminary Report on Patentability and Written Opinion issued in PCT/JP2019/010644; dated Oct. 6, 2020.

* cited by examiner

ULTRASOUND PROBE, CONTROL METHOD OF ULTRASOUND PROBE, AND ULTRASOUND PROBE INSPECTION SYSTEM

CROSS-REFERENCE TO RELATED APPLICATIONS

This application is a Continuation of PCT International Application No. PCT/JP2019/010644 filed on Mar. 14, 2019, which claims priority under 35 U.S.C. § 119(a) to Japanese Patent Application No. 2018-073183 filed on Apr. 5, 2018. The above application is hereby expressly incorporated by reference, in its entirety, into the present application.

BACKGROUND OF THE INVENTION

1. Field of the Invention

The present invention relates to an ultrasound probe and a control method of an ultrasound probe, and particularly to an ultrasound probe and a control method of an ultrasound probe which facilitate a manufacturing inspection.

Further, the invention also relates to an ultrasound probe inspection system.

2. Description of the Related Art

In the related art, in the medical field, an ultrasound diagnostic apparatus using an ultrasound image has been put to practical use. Generally, this type of ultrasound diagnostic apparatus has an ultrasound probe with a built-in transducer array, and an apparatus body connected to the ultrasound probe, transmits ultrasonic waves toward a subject from the ultrasound probe, receives ultrasound echo from the subject by the ultrasound probe, and electrically processes the received signals by the apparatus body to generate an ultrasound image.

In recent years, an ultrasound diagnostic apparatus has been developed which is intended to improve operability and mobility of an ultrasound probe by connecting the ultrasound probe and an apparatus body by wireless communication, as disclosed in JP2015-211726A, for example.

In such a wireless ultrasound diagnostic apparatus, the received signals output from the transducer array of the ultrasound probe are transmitted to the apparatus body by wireless communication, or a circuit for signal processing is built in the ultrasound probe and the received signals output from the transducer array are subjected to digital processing in the ultrasound probe and transmitted to the apparatus body by wireless communication, and thereby an ultrasound image is generated in the apparatus body.

SUMMARY OF THE INVENTION

Generally, in manufacturing an ultrasound diagnostic apparatus, an acoustic measurement inspection is performed on ultrasonic waves emitted from a transducer array of an ultrasound probe. The acoustic measurement inspection is executed in a manner that, for example, in a state where a hydrophone which is a receive-only transducer is placed in a water tank and the ultrasound probe is held so that an acoustic lens of the manufactured ultrasound probe is submerged in the water in the water tank to be above the hydrophone, ultrasonic waves are transmitted toward the hydrophone from the transducer array of the ultrasound probe, and the ultrasonic waves are received by the hydrophone.

In such an acoustic measurement inspection, acoustic signals are sampled by the hydrophone at a transmission timing and an electronic scanning timing of ultrasonic waves of the ultrasound probe, and an inspection apparatus connected to the hydrophone calculates acoustic intensity, acoustic power, and the like from the output of the hydrophone. Therefore, it is necessary to establish synchronization between the ultrasound probe and the inspection apparatus for the acoustic measurement inspection.

In a case of a wired ultrasound diagnostic apparatus in which the ultrasound probe is connected to the apparatus body by a communication cable, it is possible to establish synchronization between the ultrasound probe and the inspection apparatus via the communication cable. However, in the wireless ultrasound diagnostic apparatus as disclosed in JP2015-211726A, there is no communication cable pulled out from the ultrasound probe. In particular, since the ultrasound probe is required to be waterproof, the ultrasound probe is desired to have a closed structure, and it is difficult to pull out a signal cable from the ultrasound probe.

Further, synchronization between the ultrasound probe and the inspection apparatus can be established by transmitting and receiving synchronization signals via the wireless communication, but in this case, since a transmittable time for the synchronization signals is greatly affected by the surrounding environment, the transmission timing tends to fluctuate, and in the ultrasound diagnostic apparatus having a scanning line cycle of about 100 microseconds, it is difficult to establish synchronization having sufficient accuracy with the acoustic measurement inspection, which is a problem.

The invention is made to solve the problem in the related art, and an object thereof is to provide an ultrasound probe which is a wireless ultrasound probe and can be synchronized with an inspection apparatus with excellent accuracy without pulling out a signal cable, and a control method of the ultrasound probe.

Further, another object of the invention is to provide an ultrasound probe inspection system that performs a manufacturing inspection using such an ultrasound probe.

In order to achieve the object, an ultrasound probe according to an aspect of the invention is a wireless ultrasound probe comprising a housing; a transducer array housed in the housing; a transmission/reception unit which is housed in the housing, transmits ultrasonic wave from the transducer array, and generates a sound ray signal on the basis of a reception signal acquired by the transducer array; an image information data generation unit which is housed in the housing, and generates image information data on the basis of the sound ray signal generated by the transmission/reception unit; a wireless communication unit which is housed in the housing, and wirelessly transmits the image information data generated by the image information data generation unit; a light emission unit which is housed in the housing, and emits light to an outside of the housing; and a light emission control unit which is housed in the housing, and causes the light emission unit to emit light in synchronization with a transmission timing of the ultrasonic wave by the transmission/reception unit in a case of a manufacturing inspection.

The light emission unit may emit light having an invisible wavelength. In this case, the light having the invisible wavelength is preferably infrared light.

The light emission unit may emit light having a visible wavelength. In this case, the light emission unit may serve as an indication of power-on. In addition, the ultrasound probe may further comprise a communication state detection unit that detects a wireless communication state, and the light emission unit may serve as an indication of the wireless communication state detected by the communication state detection unit. Further, the ultrasound probe may further comprise a battery; and a remaining amount detection unit that detects a remaining amount of the battery, and the light emission unit may serve as an indication of the remaining amount of the battery detected by the remaining amount detection unit.

The ultrasound probe may further comprise a light receiving section; and a command acceptance unit that accepts a command from the outside on the basis of light acquired by the light receiving section, and the light emission control unit may be configured to cause the light emission unit to emit light on the basis of the command accepted by the command acceptance unit.

The light emission control unit may turn on and off the light emission unit in synchronization with the transmission timing of the ultrasonic wave from the transducer array for each scanning line. Further, the light emission control unit may turn on and off the light emission unit in synchronization with a start timing of each frame in ultrasound image generation, at a cycle different from an on-off cycle of the light emission unit in the transmission timing for each scanning line.

A control method of an ultrasound probe according to another aspect of the invention comprises transmitting an ultrasonic wave from a transducer array; generating a sound ray signal on the basis of a reception signal acquired by the transducer array; generating image information data on the basis of the generated sound ray signal; wirelessly transmitting the generated image information data; and causing a light emission unit to emit light in synchronization with a transmission timing of the ultrasonic wave from the transducer array in a case of a manufacturing inspection.

Further, an ultrasound probe inspection system according to still another aspect of the invention comprises the above-described ultrasound probe; and an inspection apparatus which receives the ultrasonic wave transmitted from the transducer array of the ultrasound probe, generates a synchronization signal on the basis of light emitted from the light emission unit of the ultrasound probe, and performs an inspection of the ultrasound probe on the basis of the received ultrasonic wave and the synchronization signal, in the case of the manufacturing inspection.

According to the invention, since the light emission unit that emits light to the outside of the housing and the light emission control unit that causes the light emission unit to emit light in synchronization with the transmission timing of the ultrasonic wave by the transmission/reception unit in the case of the manufacturing inspection are provided, even though the ultrasound probe is a wireless type, it is possible to establish synchronization with the inspection apparatus with excellent accuracy without pulling out a signal cable.

DESCRIPTION OF THE PREFERRED EMBODIMENTS

Hereinafter, embodiments of the invention will be described with reference to the accompanying drawings.

First Embodiment

Figure 1:
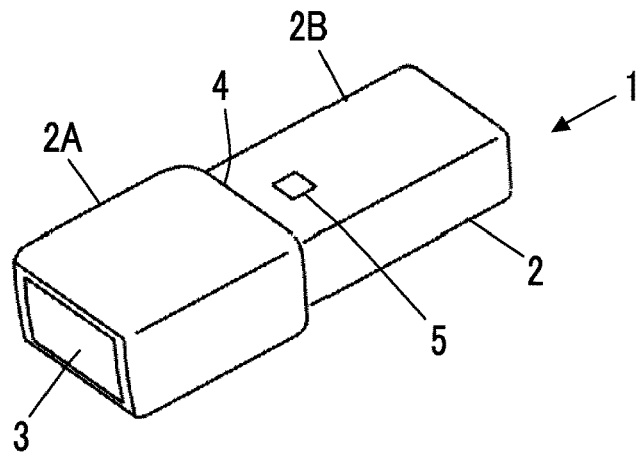
FIG. 1 is a perspective view illustrating an appearance of an ultrasound probe according to a first embodiment of the invention.

FIG. 1 illustrates an appearance of an ultrasound probe 1 according to a first embodiment of the invention. The ultrasound probe 1 has an almost rectangular prism-shaped housing 2, and an acoustic lens 3 is disposed on one end portion of the housing 2. The housing 2 is divided into a front portion 2A where the acoustic lens 3 is disposed, and a rear portion 2B on a side opposite to the acoustic lens 3, and a step portion 4 is formed between the front portion 2A and the rear portion 2B so as to surround the outer peripheral portion of the housing 2. Further, a light emission window 5 is formed in the vicinity of the step portion 4, on the rear portion 2B of the housing 2.

The housing 2 can be formed of various materials such as resin materials and metal materials.

Figure 2:
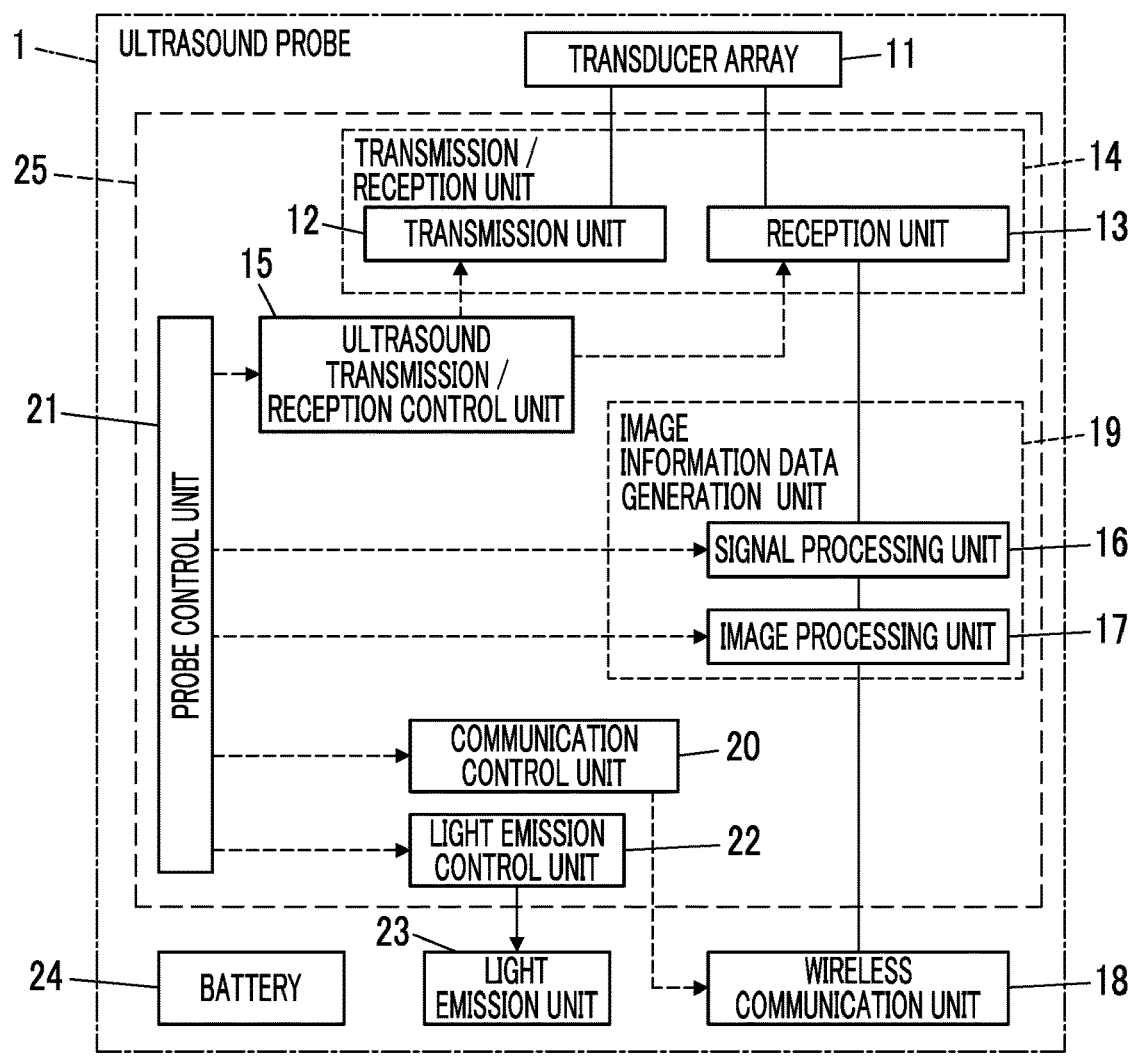
FIG. 2 is a block diagram illustrating an internal configuration of the ultrasound probe according to the first embodiment of the invention.

FIG. 2 is a block diagram illustrating an internal configuration of the ultrasound probe 1.

The ultrasound probe 1 comprises a transducer array 11, and each of a transmission unit 12 and a reception unit 13 is connected to the transducer array 11. The transmission unit 12 and the reception unit 13 form a transmission/reception unit 14, and an ultrasound transmission/reception control unit 15 is connected to the transmission unit 12 and the reception unit 13. A signal processing unit 16, an image processing unit 17, and a wireless communication unit 18 are sequentially connected to the reception unit 13. The signal processing unit 16 and the image processing unit 17 form an image information data generation unit 19.

A communication control unit 20 is connected to the wireless communication unit 18, and a probe control unit 21 is connected to the ultrasound transmission/reception control unit 15, the signal processing unit 16, the image processing unit 17, and the communication control unit 20. Further, a light emission unit 23 is connected to the probe control unit 21 via a light emission control unit 22. A battery 24 is built in the ultrasound probe 1.

The transmission unit 12, the reception unit 13, the ultrasound transmission/reception control unit 15, the signal processing unit 16, the image processing unit 17, the communication control unit 20, the probe control unit 21, and the light emission control unit 22 constitute a probe-side processor 25.

The transducer array 11 has a plurality of ultrasonic transducers arranged in a one-dimensional or two-dimensional manner. According to a drive signal supplied from the transmission unit 12, each of the transducers transmits an ultrasonic wave and receives a reflected wave from a subject to output a reception signal. For example, each transducer is formed by using an element in which electrodes are formed at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The ultrasound transmission/reception control unit 15 controls the transmission unit 12 and the reception unit 13 of the transmission/reception unit 14 to perform transmission of ultrasound beams and reception of ultrasound echoes on the basis of an inspection mode and a scanning method instructed from the probe control unit 21. Here, the inspection mode indicates any of inspection modes that can be used in the ultrasound diagnostic apparatus, such as a brightness (B) mode, a color flow (CF) mode, a pulse wave Doppler (PW) mode, and a motion (M) mode, and the scanning method indicates any one of scanning methods such as an electronic sector scanning method, an electronic linear scanning method, and an electronic convex scanning method.

The transmission unit 12 of the transmission/reception unit 14 includes, for example, a plurality of pulse generators, and the transmission unit 12 adjusts the amount of delay of each drive signal so that ultrasonic waves transmitted from the plurality of transducers of the transducer array 11 form an ultrasound beam on the basis of a transmission delay pattern selected according to a control signal from the ultrasound transmission/reception control unit 15, and supplies the obtained signals to the plurality of transducers. Thus, in a case where a pulsed or continuous-wave voltage is applied to the electrodes of the transducers of the transducer array 11, the piezoelectric body expands and contracts to generate pulsed or continuous-wave ultrasonic waves from each transducer. From the combined wave of these ultrasonic waves, an ultrasound beam is formed.

The transmitted ultrasound beam is reflected by a target, for example, a site of the subject, and propagates toward the transducer array 11. The ultrasonic waves propagating toward the transducer array 11 in this manner are received by each transducer constituting the transducer array 11. In this case, each transducer constituting the transducer array 11 expands and contracts by receiving the propagating ultrasound echo to generate electrical signals, and outputs the electrical signals to the reception unit 13.

Figure 3:
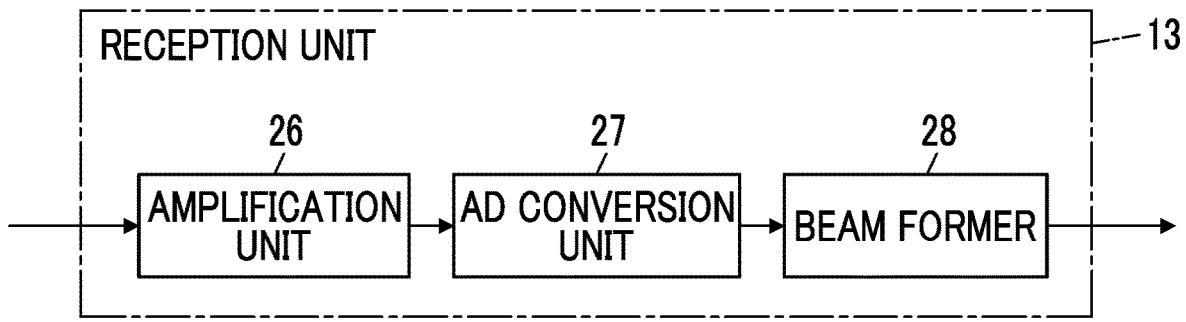
FIG. 3 is a block diagram illustrating an internal configuration of a reception unit in the ultrasound probe according to the first embodiment of the invention.

The reception unit 13 of the transmission/reception unit 14 processes the reception signals output from the transducer array 11 according to the control signal from the ultrasound transmission/reception control unit 15. As illustrated in FIG. 3, the reception unit 13 has a configuration in which an amplification unit 26, an analog digital (AD) conversion unit 27, and a beam former 28 are connected in series. The amplification unit 26 amplifies the reception signals input from each transducer constituting the transducer array 11, and transmits the amplified reception signals to the AD conversion unit 27. The AD conversion unit 27 converts the reception signals transmitted from the amplification unit 26 into digital data, and sends the data to the beam former 28. The beam former 28 performs reception focusing processing in which addition (phasing addition) is performed by giving delays to respective pieces of element data according to a set sound speed, on the basis of a reception delay pattern selected according to the control signal from the ultrasound transmission/reception control unit 15. Through the reception focusing processing, a sound ray signal with narrowed focus of the ultrasound echo is generated.

The signal processing unit 16 of the image information data generation unit 19 generates a signal, which is tomographic image information regarding tissues inside the subject, by performing envelope detection processing after correcting the attenuation of the sound ray signal generated by the beam former 28 of the reception unit 13, which is caused by the propagation distance according to the depth of the reflection position of the ultrasonic wave.

The image processing unit 17 of the image information data generation unit 19 raster-converts the signal generated by the signal processing unit 16 into the image signal according to a normal television signal scanning method, performs various kinds of necessary image processing such as brightness correction, gradation correction, sharpness correction, and color correction on the image signal generated in this manner to generate an ultrasound image signal, and then sends the ultrasound image signal as image information data to the wireless communication unit 18.

The wireless communication unit 18 includes an antenna for transmitting and receiving radio waves, modulates a carrier on the basis of the ultrasound image signal generated by the image processing unit 17 to generate a transmission signal, and transmits radio waves from the antenna by supplying the transmission signal to the antenna to perform wireless transmission of the ultrasound image signal. As the modulation method of the carrier, amplitude shift keying (ASK), phase shift keying (PSK), quadrature phase shift keying (QPSK), 16 quadrature amplitude modulation (16QAM), or the like is used.

The communication control unit 20 controls the wireless communication unit 18 such that the ultrasound image signal is transmitted with a transmission radio wave intensity set by the probe control unit 21.

The probe control unit 21 controls each unit of the ultrasound probe 1 on the basis of a program and the like stored in advance.

The light emission control unit 22 causes the light emission unit 23 to emit light in synchronization with the transmission timing of the ultrasonic wave by the transmission unit 12 of the transmission/reception unit 14 in a case of performing the manufacturing inspection on the ultrasound probe 1. Specifically, the light emission control unit 22 turns on and off the light emission unit 23 in synchronization with the transmission timing of the ultrasonic wave from the transducer array 11 for each scanning line.

The light emission unit 23 is disposed on an inner side of the light emission window 5 of the housing 2 of the ultrasound probe 1 illustrated in FIG. 1, and emits light to the outside of the housing 2 of the ultrasound probe 1 through the light emission window 5 under the control of the light emission control unit 22.

For example, a light emitting diode that emits light having an invisible wavelength such as infrared light or a light emitting diode that emits light having a visible wavelength can be used as the light emission unit 23. The light emission unit 23 is not limited to the light emitting diode, but the light emitting diode is preferable from the viewpoint of power consumption, responsiveness, brightness, and the like.

The light emission window 5 of the housing 2 of the ultrasound probe 1 is formed of a resin film having a light-transmitting property with respect to the emission wavelength of the light emission unit 23. Specifically, the light emission window 5 has a light transmittance of at least 40% or more, preferably 75% or more, more preferably 80% or more, still more preferably 90% or more in the emission wavelength range of the light emission unit 23. The light transmittance is measured using "Plastics-Determination of total luminous transmittance and reflectance" defined in JIS K 7375:2008. The light emission window 5 may be formed of a glass material in addition to the resin film.

The battery 24 is built in the ultrasound probe 1, and supplies power to each circuit of the ultrasound probe 1.

Figure 4:
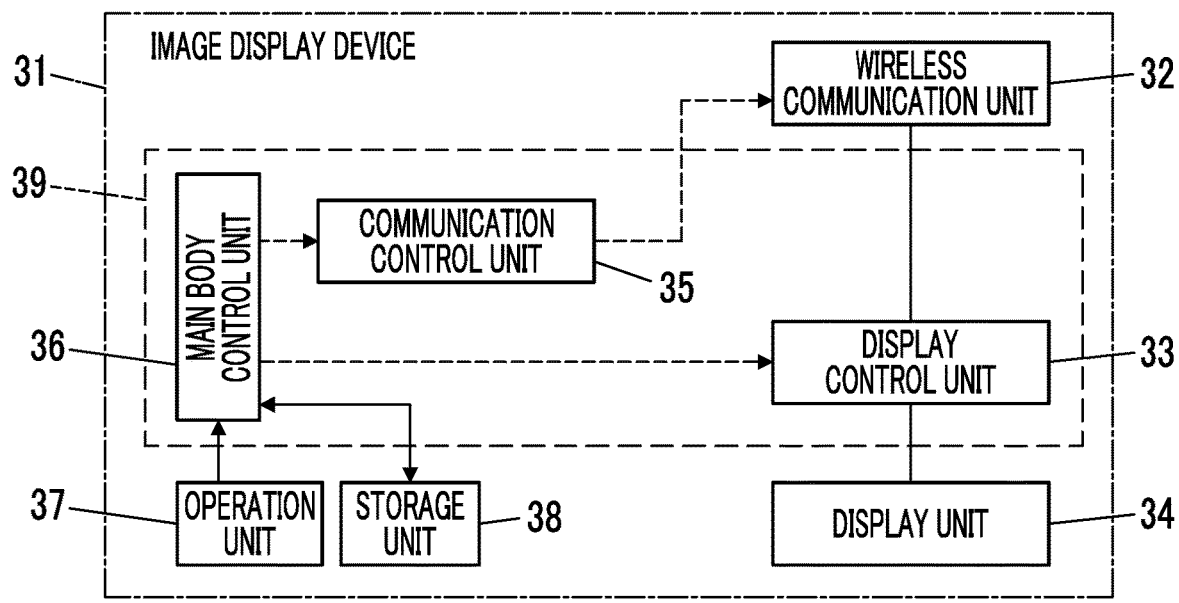
FIG. 4 is a block diagram illustrating an internal configuration of an image display device that constitutes an ultrasound system in combination with the ultrasound probe, according to the first embodiment of the invention.

Here, FIG. 4 illustrates an internal configuration of an image display device 31 that constitutes an ultrasound system in combination with the ultrasound probe 1.

The image display device 31 comprises a wireless communication unit 32, and a display control unit 33 and a display unit 34 are sequentially connected to the wireless communication unit 32. In addition, a communication control unit 35 is connected to the wireless communication unit 32, and a main body control unit 36 is connected to the display control unit 33 and the communication control unit 35. Further, an operation unit 37 and a storage unit 38 are connected to the main body control unit 36. The main body control unit 36 and the storage unit 38 are connected so as to exchange information bidirectionally.

The display control unit 33, the communication control unit 35, and the main body control unit 36 constitute an image display device-side processor 39.

The wireless communication unit 18 of the ultrasound probe 1 and the wireless communication unit 32 of the image display device 31 are connected so as to exchange information bidirectionally, and thereby the ultrasound probe 1 and the image display device 31 are connected by the wireless communication.

The wireless communication unit 32 includes an antenna for transmitting and receiving radio waves, receives the transmission signal transmitted by the wireless communication unit 18 of the ultrasound probe 1 via the antenna, and demodulates the received transmission signal to output the ultrasound image signal.

The communication control unit 35 controls the wireless communication unit 32 of the image display device 31 such that the transmission signal is received from the wireless communication unit 18 of the ultrasound probe 1.

The display control unit 33 performs predetermined processing on the ultrasound image signal demodulated by the wireless communication unit 32 and generates an image displayable on the display unit 34, under the control of the main body control unit 36.

The main body control unit 36 controls each unit of the image display device 31 on the basis of the program stored in advance in the storage unit 38 or the like and the user's operation through the operation unit 37.

The display unit 34 displays the image generated by the display control unit 33, and includes, for example, a display device such as a liquid crystal display (LCD).

The operation unit 37 is for the user to perform an input operation, and can be configured to comprise a keyboard, a mouse, a trackball, a touchpad, a touch panel, and the like.

The storage unit 38 stores an operation program and the like of the image display device 31, and recording media such as a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), or a server can be used as the storage unit 38.

Each of the probe-side processor 25 having the transmission unit 12, the reception unit 13, the ultrasound transmission/reception control unit 15, the signal processing unit 16, the image processing unit 17, the communication control unit 20, the probe control unit 21, and the light emission control unit 22 of the ultrasound probe 1, and the image display device-side processor 39 having the display control unit 33, the communication control unit 35, and the main body control unit 36 of the image display device 31 is configured by a central processing unit (CPU) and a control program causing the CPU to execute various kinds of processing, but may be configured by a digital circuit.

The transmission unit 12, the reception unit 13, the ultrasound transmission/reception control unit 15, the signal processing unit 16, the image processing unit 17, the communication control unit 20, the probe control unit 21, and the light emission control unit 22 of the probe-side processor 25 can also be configured by being integrated partially or entirely into one CPU. Similarly, the display control unit 33, the communication control unit 35, and the main body control unit 36 of the image display device-side processor 39 can be configured by being integrated partially or entirely into one CPU.

The operation of the ultrasound system consisting of the ultrasound probe 1 and the image display device 31 will be described.

First, in the ultrasound probe 1, under the control of the ultrasound transmission/reception control unit 15, the ultrasound beam is transmitted from the plurality of transducers of the transducer array 11 according to the drive signal from the transmission unit 12 of the transmission/reception unit 14, and the reception signal from each transducer which has received the ultrasound echo from the subject is output to the reception unit 13, is amplified by the amplification unit 26, is subjected to the AD conversion by the AD conversion unit 27, and is then subjected to the reception focusing processing by the beam former 28, thereby generating the sound ray signal.

The sound ray signal generated by the beam former 28 of the reception unit 13 is subjected to the attenuation correction and envelope detection processing according to the depth of the reflection position to become a signal as tomographic image information regarding the tissue inside the subject, in the signal processing unit 16 of the image information data generation unit 19, and further is raster-converted and is subjected to various kinds of necessary image processing to generate an ultrasound image signal as the image information data, in the image processing unit 17, and the ultrasound image signal is sent to the wireless communication unit 18. The ultrasound image signal is wirelessly transmitted to the image display device 31 from the wireless communication unit 18 of the ultrasound probe 1.

The ultrasound image signal wirelessly transmitted from the wireless communication unit 18 of the ultrasound probe 1 is received and demodulated by the wireless communication unit 32 of the image display device 31, and is then displayed on the display unit 34 of the image display device 31 via the display control unit 33.

In a case where such an ultrasound probe 1 is manufactured, as a manufacturing inspection, an acoustic measurement inspection of the ultrasound probe 1 is performed.

Figure 5:
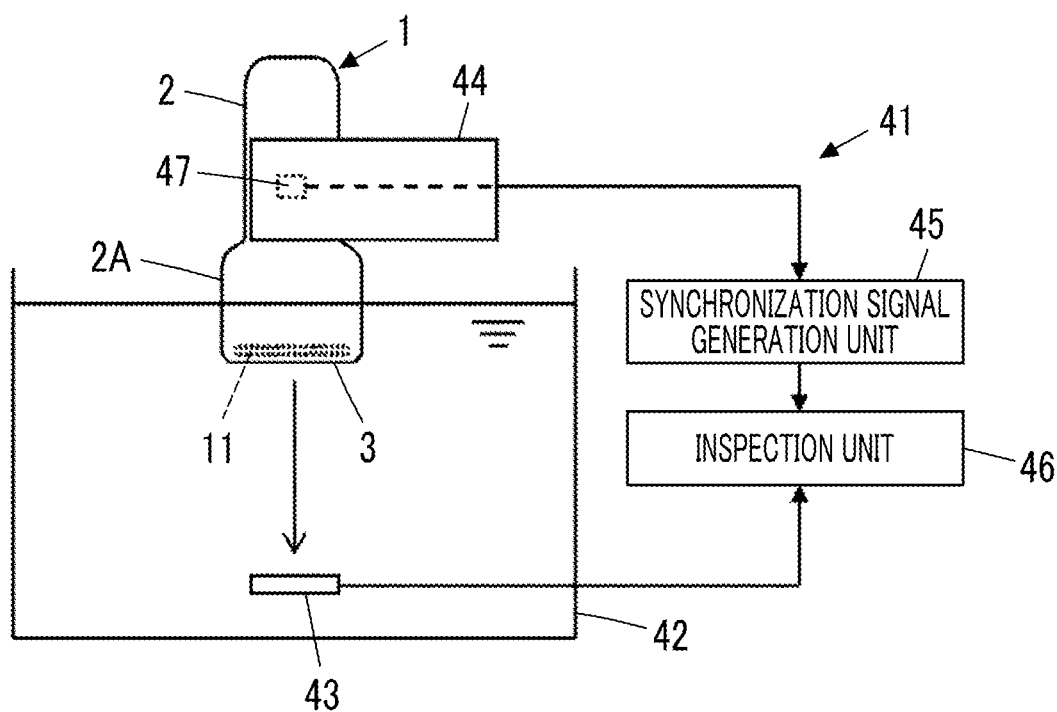
FIG. 5 is a diagram illustrating the ultrasound probe and an inspection apparatus according to the first embodiment of the invention in a case of a manufacturing inspection.

The acoustic measurement inspection is executed using an inspection apparatus 41 as illustrated in FIG. 5, for example. The inspection apparatus 41 has a hydrophone 43 disposed in the water in a water tank 42, and a probe holder 44 that holds the ultrasound probe 1. The inspection apparatus 41 further has a synchronization signal generation unit 45 connected to the probe holder 44, and an inspection unit 46 connected to the hydrophone 43 and the synchronization signal generation unit 45.

The hydrophone 43 is a receive-only transducer, has acoustic impedance close to that of water, and is suitable for measuring a sound field of ultrasonic waves in the water.

The probe holder 44 is for holding the ultrasound probe 1, and an inspection apparatus-side light receiving section 47 that receives light emitted from the light emission unit 23 of the ultrasound probe 1 is installed in the probe holder 44. For example, the inspection apparatus-side light receiving section 47 is configured by a general-purpose light-receiving element, such as a photodiode or a phototransistor, which has a light receiving sensitivity region corresponding to a wavelength range of light emitted from the light emission unit 23, and receives light which is emitted from the light emission unit 23 and is transmitted through the light emission window 5 of the housing 2, and converts the light into the electrical signal.

The synchronization signal generation unit 45 generates a synchronization signal on the basis of the electrical signal converted by the inspection apparatus-side light receiving section 47 installed in the probe holder 44.

The inspection unit 46 calculates acoustic intensity, acoustic power, and the like on the basis of the ultrasonic waves received by the hydrophone 43 and the synchronization signal generated by the synchronization signal generation unit 45, to perform the inspection of the ultrasound probe 1.

Figure 6:
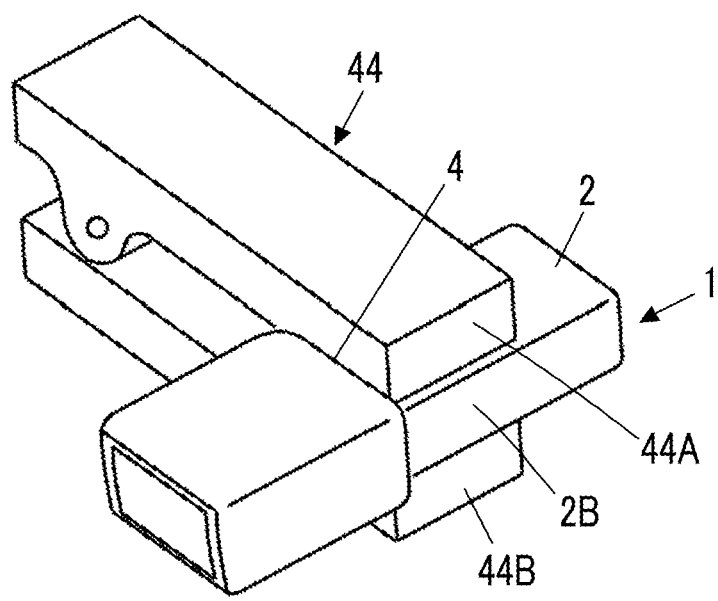
FIG. 6 is a perspective view illustrating a state in which the ultrasound probe according to the first embodiment of the invention is held by a probe holder of the inspection apparatus.

As illustrated in FIG. 6, the probe holder 44 has a pair of arm portions 44A and 44B that are biased to press each other by a spring (not illustrated), the arm portions 44A and 44B are closely attached to the outer surface of the housing 2 of the ultrasound probe 1 to interpose the rear portion 2B of the housing 2 of the ultrasound probe 1 therebetween, and thereby the ultrasound probe 1 is held by the probe holder 44. In this case, the position of the ultrasound probe 1 with respect to the probe holder 44 is set such that the step portion 4 of the housing 2 of the ultrasound probe 1 is in contact with the arm portions 44A and 44B of the probe holder 44.

Figure 7:
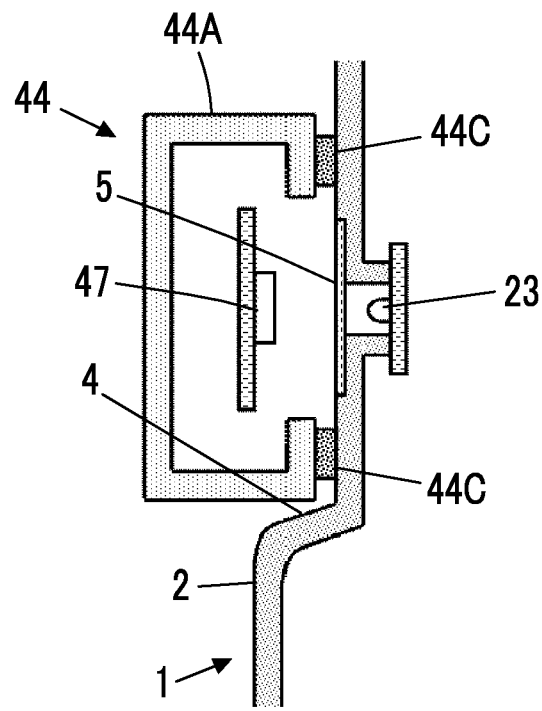
FIG. 7 is an enlarged cross-sectional view of main parts illustrating a state in which the ultrasound probe according to the first embodiment of the invention is held by the probe holder of the inspection apparatus.

As a result, as illustrated in FIG. 7, the inspection apparatus-side light receiving section 47 installed in the arm portion 44A of the probe holder 44 is at a position to face the light emission window 5 of the housing 2 of the ultrasound probe 1 held by the probe holder 44, and thereby the light emission unit 23 of the ultrasound probe 1 and the inspection apparatus-side light receiving section 47 are aligned with each other.

The light emission unit 23 is disposed in an opening portion formed in the housing 2 of the ultrasound probe 1, and is configured such that the opening portion of the housing 2 is closed and sealed by the light emission window 5. Since the opening portion of the housing 2 is closed by the light emission window 5, the waterproof property of the housing 2 of the ultrasound probe 1 is ensured.

In addition, a light shielding member 44C is disposed on the arm portion 44A of the probe holder 44, at a location where the arm portion 44A is in contact with the housing 2 of the ultrasound probe 1, and the light shielding member 44C is configured to prevent outside light from entering the inside of the arm portion 44A from a portion between the probe holder 44 and the ultrasound probe 1 in a case where the probe holder 44 holds the ultrasound probe 1. The light shielding member 44C desirably has elasticity so that a gap is not formed between the probe holder 44 and the ultrasound probe 1 in a case where the ultrasound probe 1 is held by the probe holder 44, and the light shielding member 44C can be formed of, for example, a rubber material, a resin material, or the like having light shielding properties and elasticity.

As illustrated in FIG. 5, the probe holder 44 is supported by a support device (not illustrated) such that the acoustic lens 3 disposed on the front portion 2A of the housing 2 of the ultrasound probe 1 held by the probe holder 44 is submerged in the water in the water tank 42 and faces the hydrophone 43 in the water tank 42.

In this state, the ultrasonic wave is transmitted from the transducer array 11 of the ultrasound probe 1 toward the hydrophone 43, but the light emission control unit 22 of the ultrasound probe 1 turns on and off the light emission unit 23 in synchronization with the transmission timing of the ultrasonic wave from the transducer array 11 for each scanning line. Therefore, the light emitted from the light emission unit 23 is transmitted through the light emission window 5 of the housing 2 of the ultrasound probe 1, reaches the inspection apparatus-side light receiving section 47 disposed in the arm portion 44A of the probe holder 44, and is converted into the electrical signal by the inspection apparatus-side light receiving section 47. The electrical signal converted by the inspection apparatus-side light receiving section 47 is input to the synchronization signal generation unit 45, and the synchronization signal is generated by the synchronization signal generation unit 45, and is input to the inspection unit 46.

In addition, the ultrasonic wave transmitted from the transducer array 11 of the ultrasound probe 1 reaches the hydrophone 43 in the water tank 42, and the reception signal generated by the hydrophone 43 is input to the inspection unit 46.

The inspection unit 46 calculates acoustic intensity, acoustic power, and the like on the basis of the reception signal from the hydrophone 43 and the synchronization signal input from the synchronization signal generation unit 45, and thereby the inspection of the ultrasound probe 1 is performed.

In this manner, the light emission control unit 22 of the ultrasound probe 1 causes the light emission unit 23 to emit light in synchronization with the transmission timing of the ultrasonic wave from the transducer array 11 of the ultrasound probe 1, and the inspection apparatus-side light receiving section 47 of the probe holder 44 receives the light from the light emission unit 23 of the ultrasound probe 1 so that the synchronization signal is generated by the synchronization signal generation unit 45. Thus, even though the ultrasound probe 1 is the wireless type, it is possible to establish synchronization with the inspection apparatus 41 with excellent accuracy without pulling out the signal cable from the housing 2 of the ultrasound probe 1. Therefore, in the manufacturing inspection of the ultrasound probe 1, it is possible to ensure timing stability required for high-speed transmission and reproducibility of a data acquisition timing, and it is possible to perform an inspection with high accuracy.

In the first embodiment, the light emission control unit 22 turns on and off the light emission unit 23 in synchronization with the transmission timing of the ultrasonic wave from the transducer array 11 for each scanning line, but the light emission control unit 22 may turn on and off the light emission unit 23 in synchronization with a start timing of each frame in the ultrasound image generation, at a cycle different from the on-off cycle of the light emission unit 23 in the transmission timing for each scanning line. For example, at the start of each frame, the light emission unit 23 is turned on and off at a cycle of ½ of the on-off cycle in the transmission timing for each scanning line, so that, in a case of the manufacturing inspection, the inspection unit 46 of the inspection apparatus 41 can grasp that it is the start timing of each frame and can smoothly perform the inspection of the ultrasound probe 1.

Further, in a case where the light emission unit 23 is configured by a light emitting diode that emits light with a plurality of colors in a visible wavelength, the light emission in synchronization with the transmission timing of the ultrasonic wave from the transducer array 11 for each scanning line and the light emission in synchronization with the start timing of each frame can be performed in different colors. By the inspection apparatus-side light receiving section 47 of the inspection apparatus 41 identifying the difference in color (frequency) of the light emitted from the light emission unit 23 of the ultrasound probe 1, the inspection unit 46 can discriminate whether it is the transmission timing of the ultrasonic wave from the transducer array 11 for each scanning line or the start timing of each frame.

Further, in a case where the light emission unit 23 is configured by the light emitting diode that emits light having a visible wavelength, the light emission control unit 22 can cause the light emission unit 23 to emit light so as to indicate that power supply is supplied to each circuit of the ultrasound probe 1 from the battery 24 by turning on a power switch (not illustrated) of the ultrasound probe 1. That is, the light emission unit 23 can serve as an indication of a power-on state of the ultrasound probe 1.

Figure 8:
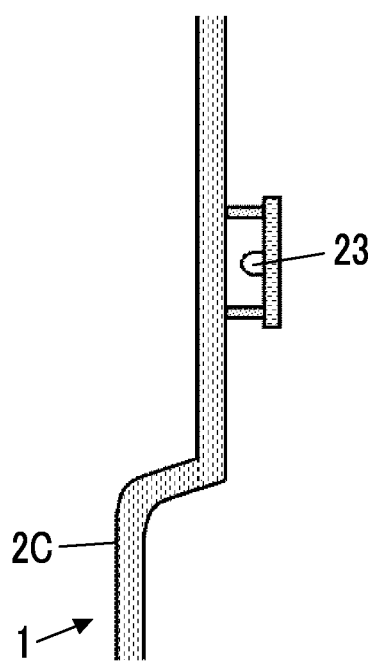
FIG. 8 is an enlarged cross-sectional view of main parts illustrating an ultrasound probe according to a modification example of the first embodiment of the invention.

In the first embodiment, the light emission unit 23 is disposed on the inner side of the light emission window 5 of the housing 2 of the ultrasound probe 1, and the light emitted from the light emission unit 23 passes through the light emission window 5 to propagate to the outside of the housing 2 of the ultrasound probe 1, but the invention is not limited thereto. As illustrated in FIG. 8, in a case where the ultrasound probe 1 comprises a housing 2C formed of a material having a light-transmitting property with respect to the emission wavelength of the light emission unit 23, the light emission unit 23 is disposed in the housing 2C without disposing the light emission window 5 on the housing 2C, and the light emitted from the light emission unit 23 can pass through the housing 2C to propagate to the outside of the ultrasound probe 1.

Figure 9:
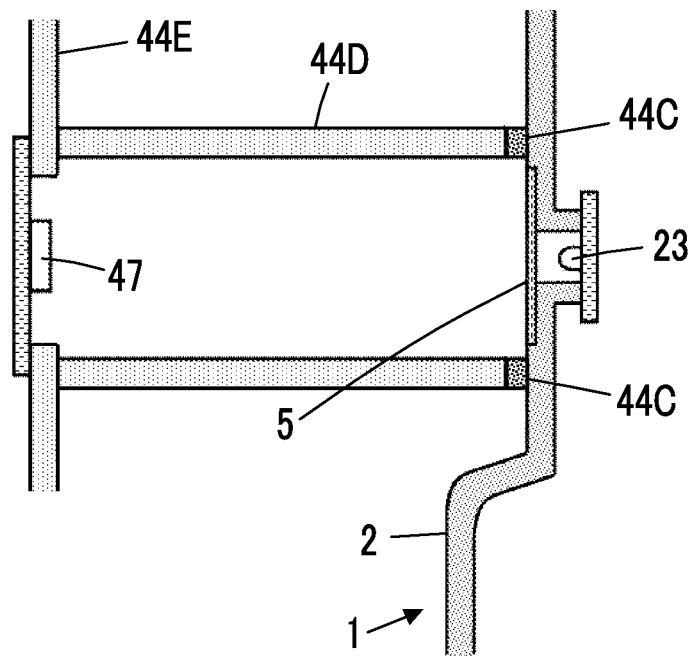
FIG. 9 is an enlarged cross-sectional view of main parts illustrating a state in which an ultrasound probe according to another modification example of the first embodiment of the invention is held by a probe holder of an inspection apparatus.

In addition, it is not necessary for the probe holder 44 to be closely attached to the outer surface of the housing 2 of the ultrasound probe 1 directly. For example, as illustrated in FIG. 9, the light emitted from the light emission unit 23 can be received by the inspection apparatus-side light receiving section 47 of a probe holder 44E via a cylindrical member 44D. Also in this case, in order to prevent the outside light from entering a portion between the cylindrical member 44D and the ultrasound probe 1, the light shielding member 44C is desirably disposed on a distal end portion of the cylindrical member 44D.

Figure 10:
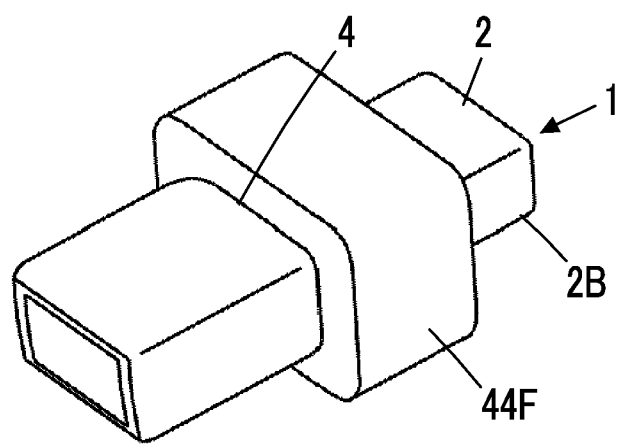
FIG. 10 is a perspective view illustrating a state in which the ultrasound probe according to the first embodiment of the invention is held by another probe holder of the inspection apparatus.

In the first embodiment, the probe holder 44 holds the ultrasound probe 1 by interposing the rear portion 2B of the housing 2 of the ultrasound probe 1 using the pair of arm portions 44A and 44B, but the invention is not limited thereto. For example, as illustrated in FIG. 10, the ultrasound probe 1 can be held by the rear portion 2B of the housing 2 of the ultrasound probe 1 being inserted into a ring-shaped probe holder 44F. The rear portion 2B of the housing 2 of the ultrasound probe 1 is inserted until the step portion 4 of the housing 2 of the ultrasound probe 1 is in contact with the ring-shaped probe holder 44F, and thereby the ultrasound probe 1 and the probe holder 44F are aligned with each other.

Second Embodiment

Figure 11:
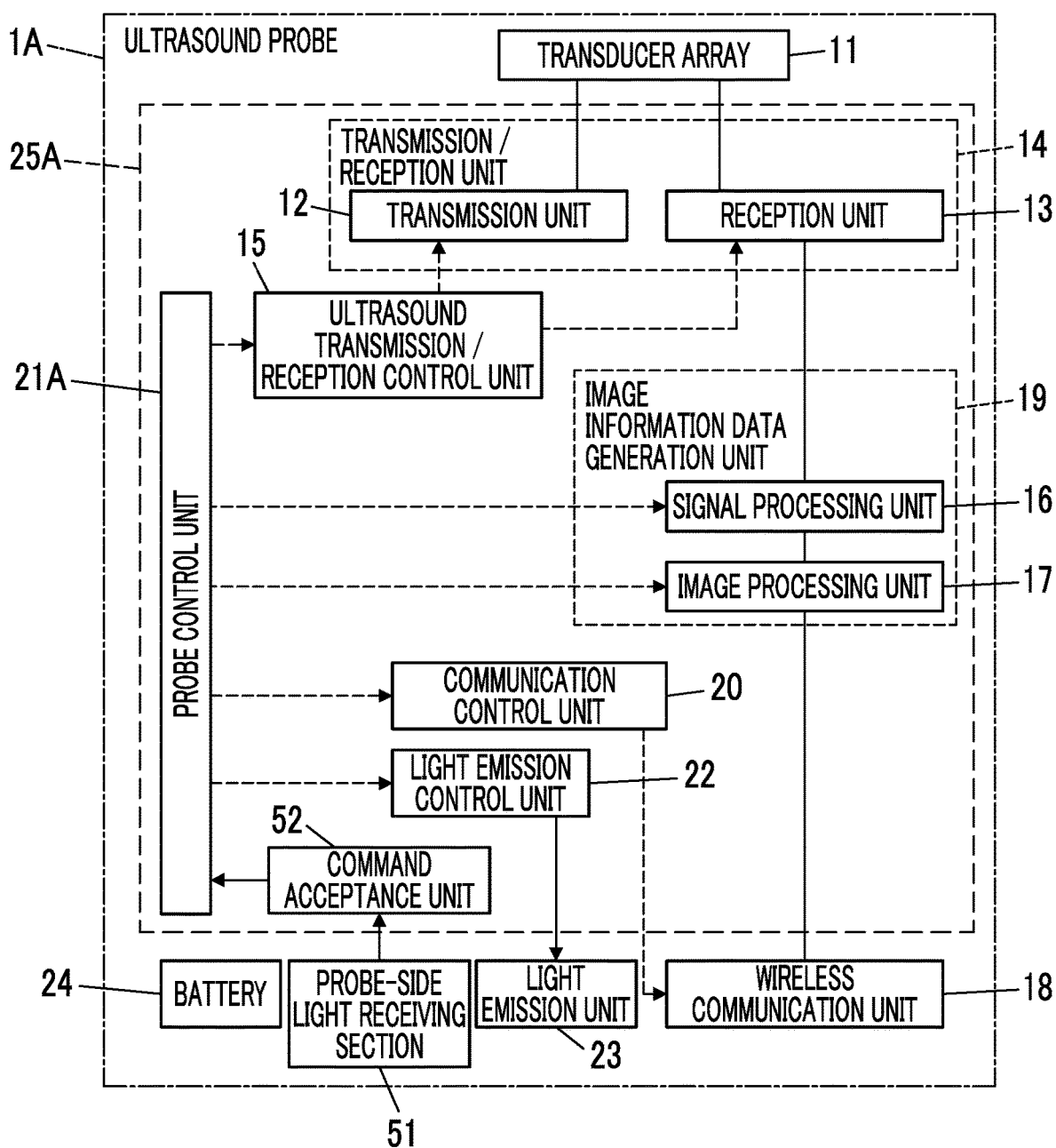
FIG. 11 is a block diagram illustrating a configuration of an ultrasound probe according to a second embodiment of the invention.

FIG. 11 illustrates an internal configuration of an ultrasound probe 1A according to a second embodiment.

The ultrasound probe 1A is different from the ultrasound probe 1 of the first embodiment illustrated in FIG. 2 in that the ultrasound probe 1A further comprises a probe-side light receiving section 51 and a command acceptance unit 52 and uses a probe control unit 21A instead of the probe control unit 21. The probe-side light receiving section 51 is connected to the command acceptance unit 52, and the command acceptance unit 52 is connected to the probe control unit 21A. The ultrasound probe 1A has the same configuration as that of the ultrasound probe 1 of the first embodiment except for the probe-side light receiving section 51, the command acceptance unit 52, and the probe control unit 21A.

Further, the transmission unit 12, the reception unit 13, the ultrasound transmission/reception control unit 15, the signal processing unit 16, the image processing unit 17, the communication control unit 20, the probe control unit 21A, the light emission control unit 22, and the command acceptance unit 52 constitute a probe-side processor 25A.

The probe-side light receiving section 51 is for receiving light emitted from the outside of the ultrasound probe 1A, is configured by, for example, a light-receiving element such as a photodiode or a phototransistor, and receives light emitted from the outside of the ultrasound probe 1A to convert the light into the electrical signal.

The command acceptance unit 52 accepts a command from the outside on the basis of the electrical signal converted by the probe-side light receiving section 51, and transfers the command to the probe control unit 21A.

Since the ultrasound probe 1A comprises the probe-side light receiving section 51 and the command acceptance unit 52, the probe control unit 21A can be operated according to a command using light from the outside of the ultrasound probe 1A, and for example, in a case of the manufacturing inspection of the ultrasound probe 1A, it is possible to instruct to cause the light emission unit 23 to emit light in synchronization with the transmission timing of the ultrasonic wave, from the outside of the ultrasound probe 1A. In addition, instructions regarding various operations can be issued from the outside of the ultrasound probe 1A via the probe-side light receiving section 51 and the command acceptance unit 52.

Third Embodiment

Figure 12:
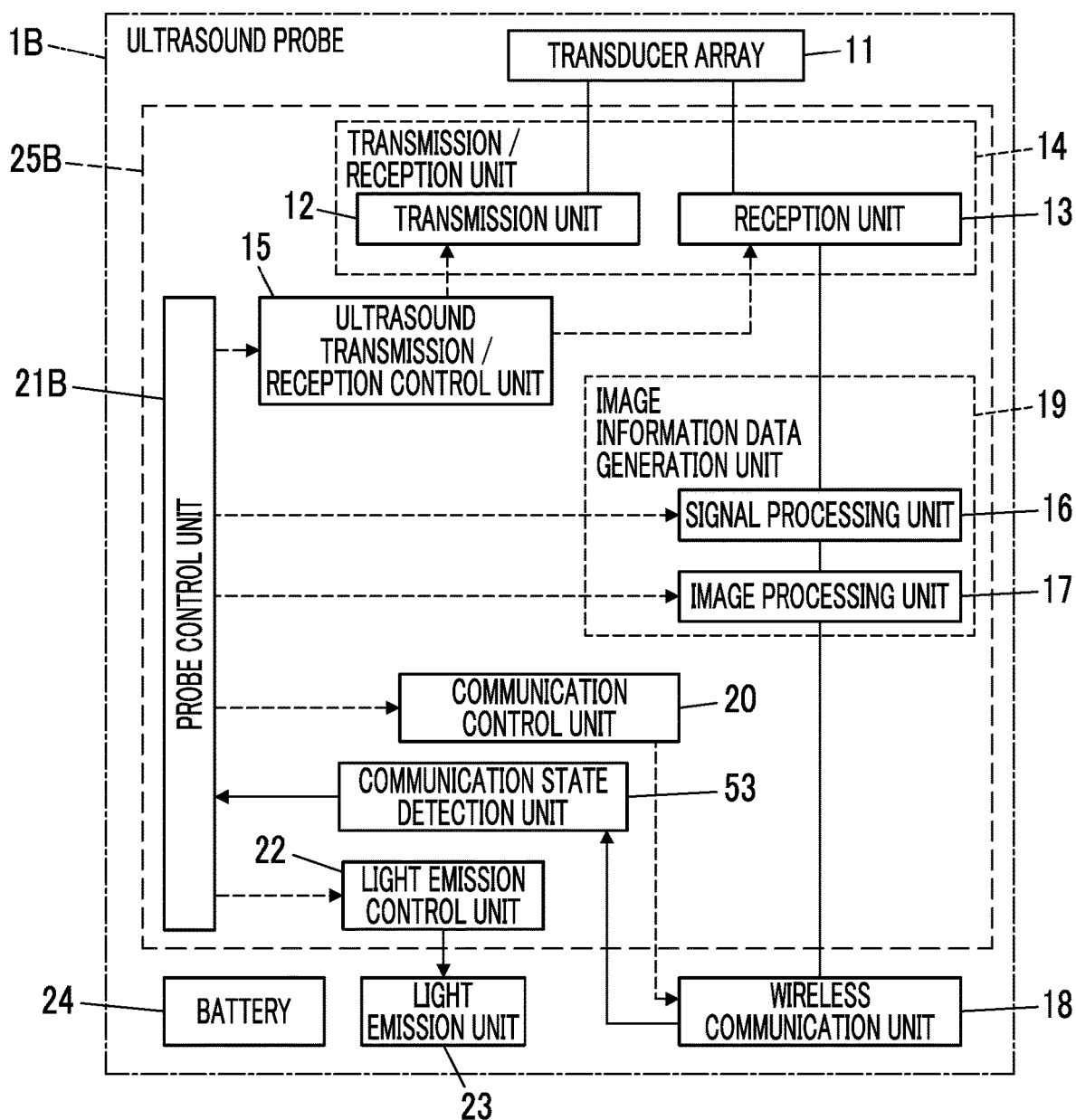
FIG. 12 is a block diagram illustrating a configuration of an ultrasound probe according to a third embodiment of the invention.

FIG. 12 illustrates an internal configuration of an ultrasound probe 1B according to a third embodiment.

The ultrasound probe 1B is different from the ultrasound probe 1 of the first embodiment illustrated in FIG. 2 in that the ultrasound probe 1B further comprises a communication state detection unit 53 connected to the wireless communication unit 18 and uses a probe control unit 21B instead of the probe control unit 21. The communication state detection unit 53 is connected to the probe control unit 21B. The ultrasound probe 1B has the same configuration as that of the ultrasound probe 1 of the first embodiment except for the communication state detection unit 53 and the probe control unit 21B.

Further, the transmission unit 12, the reception unit 13, the ultrasound transmission/reception control unit 15, the signal processing unit 16, the image processing unit 17, the communication control unit 20, the probe control unit 21B, the light emission control unit 22, and the communication state detection unit 53 constitute a probe-side processor 25B.

The communication state detection unit 53 detects a wireless communication state between the wireless communication unit 18 and the wireless communication unit 32 of the image display device 31, and outputs the detected wireless communication state to the probe control unit 21B.

In the third embodiment, the light emission unit 23 is configured by a light emitting diode that emits light having a visible wavelength.

The probe control unit 21B can cause the light emission unit 23 to emit light by the light emission control unit 22 on the basis of the wireless communication state detected by the communication state detection unit 53. For example, in a case where the wireless communication state detected by the communication state detection unit 53 is a state in which normal wireless communication can be performed between the ultrasound probe 1B and the image display device 31, the probe control unit 21B causes the light emission unit 23 to emit light by the light emission control unit 22. Thereby, the user checks the emission of light having a visible wavelength from the light emission unit 23, and thereby can grasp that the wireless transmission of the ultrasound image signal generated by the ultrasound probe 1B to the image display device 31 and the display of the ultrasound image in the image display device 31 can be performed.

That is, the light emission unit 23 can serve as an indication of the wireless communication state.

Fourth Embodiment

Figure 13:
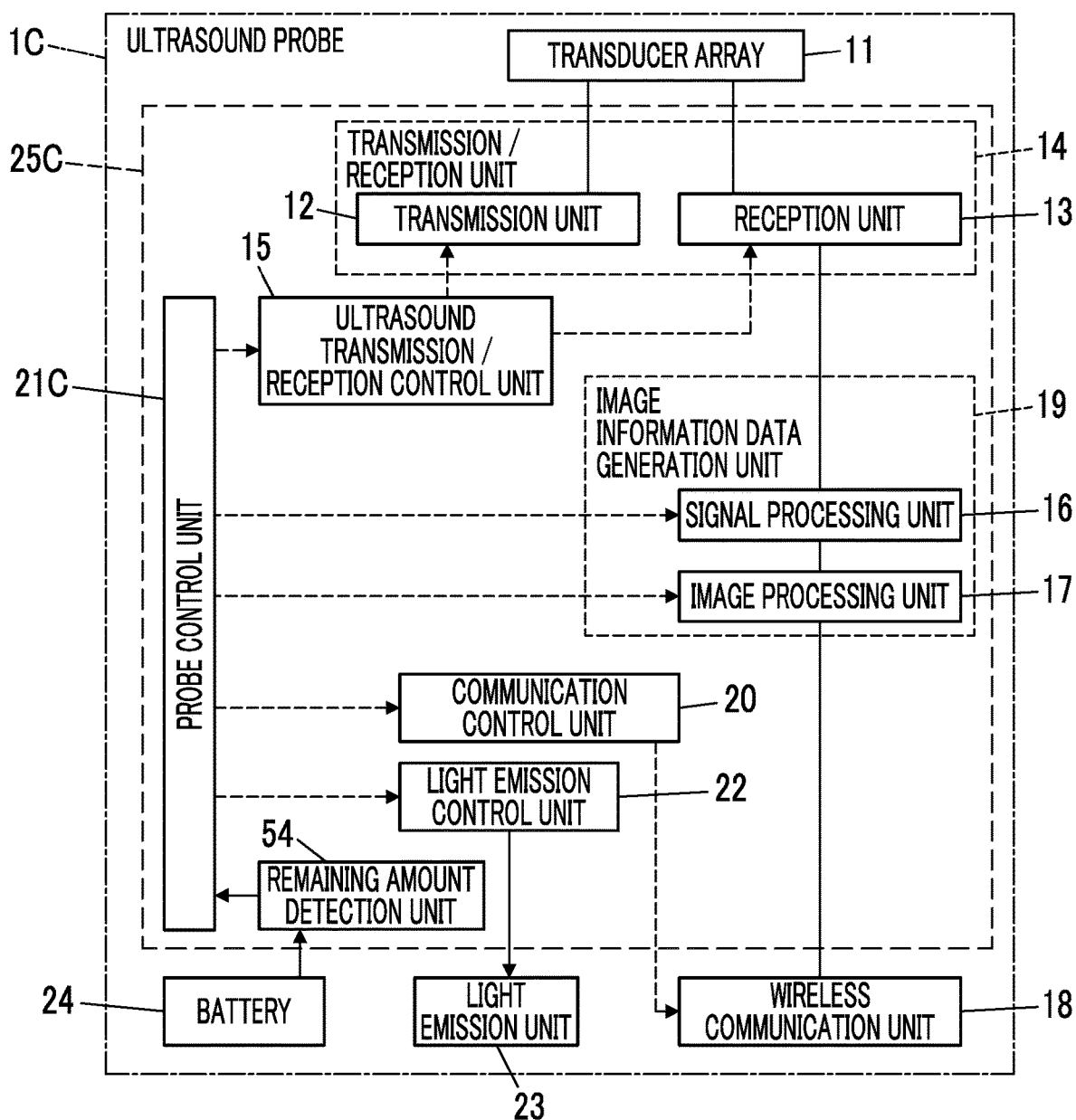
FIG. 13 is a block diagram illustrating a configuration of an ultrasound probe according to a fourth embodiment of the invention.

FIG. 13 illustrates an internal configuration of an ultrasound probe 1C according to a fourth embodiment.

The ultrasound probe 1C is different from the ultrasound probe 1 of the first embodiment illustrated in FIG. 2 in that the ultrasound probe 1C further comprises a remaining amount detection unit 54 connected to the battery 24 and uses a probe control unit 21C instead of the probe control unit 21. The remaining amount detection unit 54 is connected to the probe control unit 21C. The ultrasound probe 1C has the same configuration as that of the ultrasound probe 1 of the first embodiment except for the remaining amount detection unit 54 and the probe control unit 21C.

Further, the transmission unit 12, the reception unit 13, the ultrasound transmission/reception control unit 15, the signal processing unit 16, the image processing unit 17, the communication control unit 20, the probe control unit 21C, the light emission control unit 22, and the remaining amount detection unit 54 constitute a probe-side processor 25C.

The remaining amount detection unit 54 detects a remaining amount of the battery 24 that supplies power to each circuit of the ultrasound probe 1C, and outputs the detected remaining amount to the probe control unit 21C.

In the fourth embodiment, the light emission unit 23 is configured by a light emitting diode that emits light having a visible wavelength.

The probe control unit 21C can cause the light emission unit 23 to emit light by the light emission control unit 22 on the basis of the remaining amount of the battery 24 detected by the remaining amount detection unit 54. For example, in a case where the remaining amount of the battery 24 detected by the remaining amount detection unit 54 is lower than a predetermined remaining amount, the probe control unit 21C causes the light emission unit 23 to emit light by the light emission control unit 22. Thereby, the user checks the emission of light having a visible wavelength from the light emission unit 23, and thereby can grasp that the remaining amount of the battery 24 is lower than the predetermined remaining amount and it is necessary to charge the battery 24 or replace the battery 24.

That is, the light emission unit 23 can serve as an indication of the remaining amount of the battery 24.

Fifth Embodiment

Figure 14:
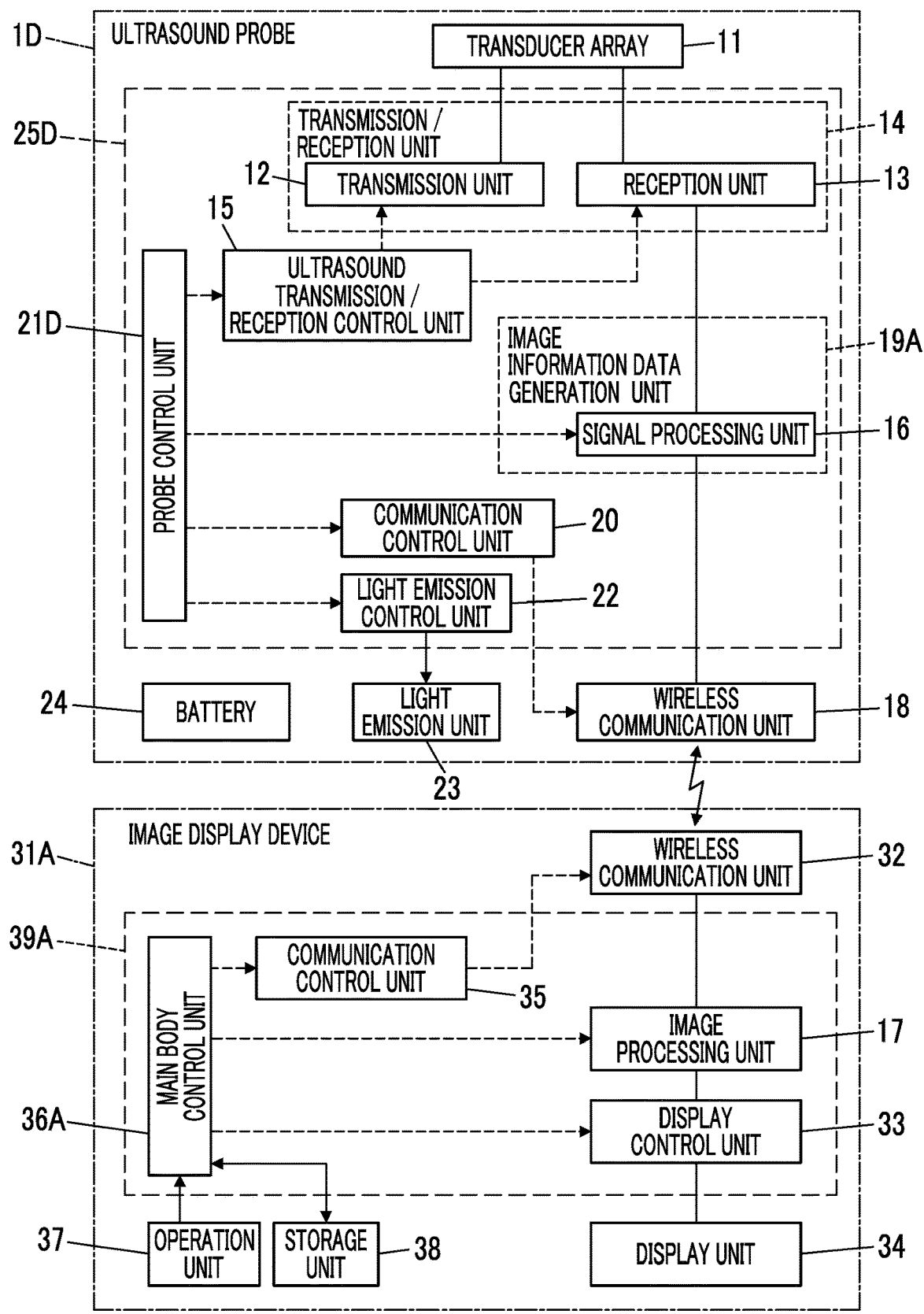
FIG. 14 is a block diagram illustrating a configuration of an ultrasound system using an ultrasound probe according to a fifth embodiment of the invention.

FIG. 14 illustrates a configuration of an ultrasound system using an ultrasound probe 1D according to a fifth embodiment.

The ultrasound probe 1D is different from the ultrasound probe 1 of the first embodiment illustrated in FIG. 2 in that the ultrasound probe 1D uses an image information data generation unit 19A having only the signal processing unit 16, instead of the image information data generation unit 19 having the signal processing unit 16 and the image processing unit 17, and uses a probe control unit 21D instead of the probe control unit 21. The signal processing unit 16 is directly connected to the wireless communication unit 18. The ultrasound probe 1D has the same configuration as that of the ultrasound probe 1 of the first embodiment except for the image information data generation unit 19A and the probe control unit 21D.

The transmission unit 12, the reception unit 13, the ultrasound transmission/reception control unit 15, the signal processing unit 16, the communication control unit 20, the probe control unit 21D, and the light emission control unit 22 constitute a probe-side processor 25D.

An image display device 31A that constitutes the ultrasound system in combination with the ultrasound probe 1D is different from the image display device 31 of the first embodiment illustrated in FIG. 4 in that the image processing unit 17 is connected between the wireless communication unit 32 and the display control unit 33 and a main body control unit 36A is used instead of the main body control unit 36. The image display device 31A has the same configuration as that of the image display device 31 of the first embodiment except for the image processing unit 17 and the main body control unit 36A.

The image processing unit 17, the display control unit 33, the communication control unit 35, and the main body control unit 36A constitute an image display device-side processor 39A.

The image processing unit 17 of the image display device 31A is the same as the image processing unit 17 used in the ultrasound probe 1 of the first embodiment.

At the time of the operation of the ultrasound system consisting of the ultrasound probe 1D and the image display device 31A, first, in the ultrasound probe 1D, under the control of the ultrasound transmission/reception control unit 15, the ultrasound beam is transmitted from the plurality of transducers of the transducer array 11 according to the drive signal from the transmission unit 12 of the transmission/reception unit 14, and the reception signal from each transducer which has received the ultrasound echo from the subject is output to the reception unit 13, is amplified by the amplification unit 26, is subjected to the AD conversion by the AD conversion unit 27, and is then subjected to the reception focusing processing by the beam former 28, thereby generating the sound ray signal.

The sound ray signal generated by the beam former 28 of the reception unit 13 is subjected to the attenuation correction and envelope detection processing according to the depth of the reflection position to become a signal as tomographic image information regarding the tissue inside the subject, in the signal processing unit 16 of the image information data generation unit 19A, and this signal is sent as the image information data to the wireless communication unit 18. The image information data is wirelessly transmitted to the image display device 31A from the wireless communication unit 18 of the ultrasound probe 1D.

The image information data wirelessly transmitted from the wireless communication unit 18 of the ultrasound probe 1D is received and demodulated by the wireless communication unit 32 of the image display device 31A, and then is raster-converted and is subjected to various kinds of necessary image processing to generate an ultrasound image signal in the image processing unit 17. The ultrasound image signal generated by the image processing unit 17 is sent to the display unit 34 via the display control unit 33, and an ultrasound image is displayed on the display unit 34.

In a case of the manufacturing inspection of the ultrasound probe 1D, the acoustic measurement inspection is performed in the same manner as in the ultrasound probe 1 of the first embodiment. That is, as illustrated in FIG. 5, the probe holder 44 is supported by a support device (not illustrated) such that the acoustic lens 3 disposed on the front portion 2A of the housing 2 of the ultrasound probe 1D held by the probe holder 44 is submerged in the water in the water tank 42 and faces the hydrophone 43 in the water tank 42.

In this state, the ultrasonic wave is transmitted from the transducer array 11 of the ultrasound probe 1D toward the hydrophone 43, but the light emission control unit 22 of the ultrasound probe 1D turns on and off the light emission unit 23 in synchronization with the transmission timing of the ultrasonic wave from the transducer array 11 for each scanning line. Therefore, the light emitted from the light emission unit 23 is transmitted through the light emission window 5 of the housing 2 of the ultrasound probe 1D, reaches the inspection apparatus-side light receiving section 47 disposed in the arm portion 44A of the probe holder 44, and is converted into the electrical signal by the inspection apparatus-side light receiving section 47. The electrical signal converted by the inspection apparatus-side light receiving section 47 is input to the synchronization signal generation unit 45, and the synchronization signal is generated by the synchronization signal generation unit 45, and is input to the inspection unit 46.

In addition, the ultrasonic wave transmitted from the transducer array 11 of the ultrasound probe 1D reaches the hydrophone 43 in the water tank 42, and the reception signal generated by the hydrophone 43 is input to the inspection unit 46.

The inspection unit 46 calculates acoustic intensity, acoustic power, and the like on the basis of the reception signal from the hydrophone 43 and the synchronization signal input from the synchronization signal generation unit 45, and thereby the inspection of the ultrasound probe 1D is performed.

In this manner, the light emission control unit 22 of the ultrasound probe 1D causes the light emission unit 23 to emit light in synchronization with the transmission timing of the ultrasonic wave from the transducer array 11 of the ultrasound probe 1D, and the inspection apparatus-side light receiving section 47 of the probe holder 44 receives the light from the light emission unit 23 of the ultrasound probe 1D so that the synchronization signal is generated by the synchronization signal generation unit 45. Thus, even though the ultrasound probe 1D is the wireless type, it is possible to establish synchronization with the inspection apparatus 41 with excellent accuracy without pulling out the signal cable from the housing 2 of the ultrasound probe 1D.

Thus, in the first embodiment, after the attenuation correction and envelope detection processing are performed by the signal processing unit 16 of the image information data generation unit 19, and then the ultrasound image signal raster-converted by the image processing unit 17 is wirelessly transmitted as the image information data to the image display device 31 from the wireless communication unit 18, and in the fifth embodiment, the signal subjected to the attenuation correction and envelope detection processing by the signal processing unit 16 of the image information data generation unit 19A is wirelessly transmitted as the image information data to the image display device 31A from the wireless communication unit 18, but the image information data wirelessly transmitted from the ultrasound probe 1 to the image display device 31 and the image information data wirelessly transmitted from the ultrasound probe 1D to the image display device 31A are preferably signals after detection. However, the image information data is not limited to the signal after detection.

The ultrasound probes 1, 1A, 1B, 1C, and 1D according to the first to fifth embodiments can constitute an ultrasound system in combination with the image display devices 31 and 31A in which a touch sensor is combined with the display unit 34 and the touch sensor is used as the operation unit 37. Such an ultrasound system is extremely effective for outdoor diagnosis in a case of emergency treatment and the like.

EXPLANATION OF REFERENCES 1, 1A, 1B, 1C, 1D: ultrasound probe
2, 2C: housing
2A: front portion
2B: rear portion
3: acoustic lens
4: step portion
5: light emission window
11: transducer array
12: transmission unit
13: reception unit
14: transmission/reception unit 15: ultrasound transmission/reception control unit
16: signal processing unit
17: image processing unit
18: wireless communication unit
19, 19A: image information data generation unit
20: communication control unit
21, 21A, 21B, 21C, 21D: probe control unit
22: light emission control unit
23: light emission unit
24: battery
25, 25A, 25B, 25C, 25D: probe-side processor
26: amplification unit
27: AD conversion unit
28: beam former
31, 31A: image display device
32: wireless communication unit
33: display control unit
34: display unit
35: communication control unit
36, 36A: main body control unit
37: operation unit
38: storage unit
39, 39A: image display device-side processor
41: inspection apparatus
42: water tank
43: hydrophone
44, 44E, 44F: probe holder
44A, 44B: arm portion
44C: light shielding member
44D: cylindrical member
45: synchronization signal generation unit
46: inspection unit
47: inspection apparatus-side light receiving section
51: probe-side light receiving section
52: command acceptance unit
53: communication state detection unit
54: remaining amount detection unit

What is claimed is:

1. A wireless ultrasound probe comprising:
a housing;
a transducer array housed in the housing;
a light emission device which is housed in the housing, and emits light to an outside of the housing; and
a controller which is housed in the housing, the controller being configured to:
  transmit ultrasonic wave from the transducer array, and generate a sound ray signal on the basis of a reception signal acquired by the transducer array;
  generate image information data on the basis of the sound ray signal generated;
  wirelessly transmit the image information data generated; and
  cause the light emission device to emit light in synchronization with a transmission timing of the ultrasonic wave in a case of a manufacturing inspection,
wherein the controller turns on and off the light emission device in synchronization with the transmission timing of the ultrasonic wave from the transducer array for each scanning line, and
wherein the controller turns on and off the light emission device in synchronization with a start timing of each frame in ultrasound image generation, at a cycle different from an on-off cycle of the light emission device in the transmission timing for each scanning line.

2. The ultrasound probe according to claim 1,
wherein the light emission device emits light having an invisible wavelength.

3. The ultrasound probe according to claim 2,
wherein the light having the invisible wavelength is infrared light.

4. The ultrasound probe according to claim 1,
wherein the light emission device emits light having a visible wavelength.

5. The ultrasound probe according to claim 4,
wherein the light emission device serves as an indication of power-on of the ultrasound probe.

6. The ultrasound probe according to claim 5,
wherein the controller detects a wireless communication state, and
the light emission device indicates the wireless communication state detected by the controller.

7. The ultrasound probe according to claim 6, further comprising a battery,
wherein the controller detects a remaining amount of the battery, and
the light emission device indicates the remaining amount of the battery detected by the controller.

8. The ultrasound probe according to claim 5, further comprising a battery,
wherein the controller detects a remaining amount of the battery, and
the light emission device indicates the remaining amount of the battery detected by the controller.

9. The ultrasound probe according to claim 4,
wherein the controller detects a wireless communication state, and
the light emission device indicates the wireless communication state detected by the controller.

10. The ultrasound probe according to claim 9, further comprising a battery,
wherein the controller detects a remaining amount of the battery, and
the light emission device indicates the remaining amount of the battery detected by the controller.

11. The ultrasound probe according to claim 9, further comprising a probe-side light receiving device,
wherein the controller accepts a command from the outside of the housing on the basis of light acquired by the probe-side light receiving device, and causes the light emission device to emit light on the basis of the command accepted.

12. The ultrasound probe according to claim 4, further comprising a battery,
wherein the controller detects a remaining amount of the battery, and
the light emission device indicates the remaining amount of the battery detected by the controller.

13. The ultrasound probe according to claim 1, further comprising a probe-side light receiving device,
wherein the controller accepts a command from the outside of the housing on the basis of light acquired by the probe-side light receiving device, and causes the light emission device to emit light on the basis of the command accepted.

14. A control method of an ultrasound probe, comprising:
transmitting an ultrasonic wave from a transducer array;
generating a sound ray signal on the basis of a reception signal acquired by the transducer array;
generating image information data on the basis of the generated sound ray signal;
wirelessly transmitting the generated image information data;

causing a light emission device to emit light in synchronization with a transmission timing of the ultrasonic wave from the transducer array in a case of a manufacturing inspection;

turning on and off the light emission device in synchronization with the transmission timing of the ultrasonic wave from the transducer array for each scanning line; and turning on and off the light emission device in synchronization with a start timing of each frame in ultrasound image generation, at a cycle different from an on-off cycle of the light emission device in the transmission timing for each scanning line.

15. An ultrasound probe inspection system comprising:
a wireless ultrasound probe; and
an inspection apparatus,
wherein the wireless ultrasound probe comprises:
a housing;
a transducer array housed in the housing;
a light emission device which is housed in the housing, and emits light to an outside of the housing; and
a controller which is housed in the housing, the controller being configured to:
transmit ultrasonic wave from the transducer array, and generate a sound ray signal on the basis of a reception signal acquired by the transducer array;
generate image information data on the basis of the sound ray signal generated;
wirelessly transmit the image information data generated; and
cause the light emission device to emit light in synchronization with a transmission timing of the ultrasonic wave in a case of a manufacturing inspection,
wherein the inspection apparatus receives the ultrasonic wave transmitted from the transducer array of the ultrasound probe, generates a synchronization signal on the basis of light emitted from the light emission device of the ultrasound probe, and performs an inspection of the ultrasound probe on the basis of the received ultrasonic wave and the synchronization signal, in the case of the manufacturing inspection.

16. The ultrasound probe inspection system according to claim 15,
wherein the inspection apparatus has
a probe holder that holds the ultrasound probe, and
an inspection apparatus-side light receiving device that is installed in the probe holder and receives light emitted from the light emission device of the ultrasound probe.

* * * * *